United States Patent [19]

Sakai

[11] Patent Number: 4,803,078
[45] Date of Patent: Feb. 7, 1989

[54] WOUND DRESSING

[75] Inventor: Mari Sakai, Okayama, Japan

[73] Assignee: Japan Gore-Tex, Inc., Tokyo, Japan

[21] Appl. No.: 172,792

[22] Filed: Mar. 28, 1988

[30] Foreign Application Priority Data

Jun. 16, 1987 [JP] Japan .................................. 62-0913[U]

[51] Int. Cl.$^4$ ................................................ A61K 9/70
[52] U.S. Cl. ...................................... 424/445; 424/443;
128/155; 128/156
[58] Field of Search ...................... 424/443, 444, 445;
128/155, 156

[56] References Cited

U.S. PATENT DOCUMENTS 4,373,519  2/1983  Orrede et al. .................... 128/155
4,664,105  5/1987  Dautzenberg et al. ............ 604/367

Primary Examiner—George F. Lesmes
Assistant Examiner—L. R. Horne
Attorney, Agent, or Firm—Mortenson & Uebler

[57] ABSTRACT

A wound dressing is provided comprising a layer of chitin affixed to a layer of porous, expanded polytetrafluoroethylene (PTFE). The chitin may be laminated to the PTFE or it may penetrate into and be impregnated in the porous PTFE layer. The composite preferably has a pressure sensitive adhesive applied in a dot pattern on its surface to enable application and securing of the dressing over a wound.

8 Claims, 1 Drawing Sheet

WOUND DRESSING

BACKGROUND OF THE INVENTION

The present invention concerns a wound-covering material or wound dressing. The object of the present invention is: (a) to insure antibacterial barrier properties and waterproof properties in a covering material which is applied to cuts, burns and other wounds in order to protect such wounds; (b) to insure acceptable compatibility with the wound; (c) to maintain air and water vapor permeability; and (d) to prevent invasion by body tissues so that stripping of the covering material from the wound is facilitated.

The present invention may be applied to covering materials for cuts and other wounds, artificial skin and other biocompatible materials.

Generally, woven or knitted fabrics, papers and films coated with pharmocologically effective compounds have been used in the past as materials for covering wounds. In addition, biological materials such as collagen films, chitin films, fibrin films and pigskin have also been used as such covering materials. In addition, soft synthetic products such as silicone rubber films have been used to some extent. See, generally, the materials disclosed in the following U.S. Pat. Nos. 4,651,725; 4,664,105; 4,689,399; 3,431,907; 3,849,238; 4,233,360; and 4,657,006.

In the case of the abovementioned conventional covering materials, invasion of the wound by bacteria and water from the outside generally cannot be completely prevented. Furthermore, materials which can prevent invasion of the wound do not generally possess air permeability or moisture vapor permeability. As a result, the affected area may become inflamed, thus retarding the healing process and subjecting the patient to discomfort. Moreover, such wound covering materials may adhere to the wound, and thus further injure the wound every time the covering material is changed. The patient using the covering material is thus subjected to additional suffering.

SUMMARY OF THE INVENTION

A wound dressing is provided comprising a layer of chitin affixed to a layer of porous, expanded polytetrafluroethylene (PTFE). The chitin may be laminated to the PTFE or it may penetrate into and be impregnated in the porous PTFE layer. The dressing preferably has a pressure sensitive adhesive applied in a dot pattern on its surface, thereby providing means to apply and secure the dressing over a wound. The porous, expanded PTFE has a microstructure of nodes interconnected by fibrils wherein fibril lengths preferably range from about 0.01 to about 1.0 micrometers. A layer of a water-absorbing macromolecular material may be interposed between the chitin layer and the PTFE layer. The water-absorbing macromolecular material preferably is polyvinylalcohol or an acrylic acid graft-polymerized starch which will absorb blood and other liquids.

DETAILED DESCRIPTION OF THE INVENTION AND PREFERRED EMBODIMENTS WITH REFERENCE TO THE DRAWINGS

A wound dressing is provided comprising a layer of chitin affixed to a layer of porous, expanded polytetrafluoroethylene (PTFE). The chitin may be laminated to the PTFE or it may penetrate and be impregnated in the porous PTFE layer. The composite preferably has a pressure sensitive adhesive applied in a dot pattern on its surface to enable application and securing of the dressing over a wound.

Specifically, the present invention provides a wound covering or a wound dressing material which is characterized by the fact that a chitin layer is applied to a porous, expanded polytetrafluoroethylene film.

The chitin layer decomposes and is absorbed by the wound. The abovementioned porous, expanded polytetrafluoroethylene film is applied so that it fits appropriately over the chitin and over the area of the wound.

The micropores of the PTFE film insure air and water vapor permeability. Moreover, the micropores prevent invasion of the wound by bacteria and dust, and act in combination with the water-repellent nature of the material itself to provide waterproof characteristics. Furthermore, the covering material can easily be peeled from the wound even in cases where all of the chitin has been decomposed and absorbed. The porous, expanded PTFE material and its method of manufacture are disclosed in U.S. Pat. No. 3,953,566.

The following is a description of examples of the present invention with reference to the accompanying drawings.

Figure 1:
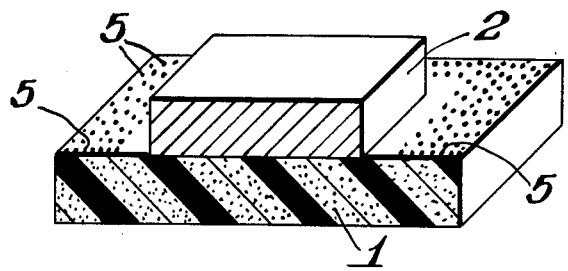
FIG. 1 is a perspective view, partly in cross-section, of one embodiment of the wound dressing according to the invention.
Figure 2:
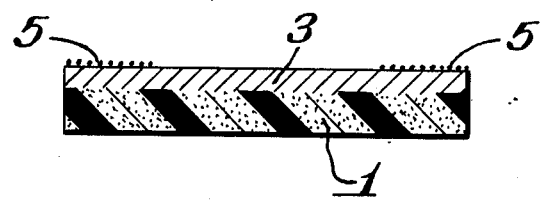
FIG. 2 is a cross-sectional view of another embodiment of the invention.

First, in regard to the manner of application of the aforementioned chitin 2 to the aforementioned porous, expanded polytetrafluoroethylene film 1, the chitin 2 may be laminated with the porous film as shown in FIG. 1 or a chitin-impregnated layer 3 may be formed as shown in FIG. 2. The chitin layer preferably is affixed to the PTFE layer as shown in FIG. 1 as follows: (1) the chitin layer is laminated onto the PTFE layer by an adhesive which is harmless to living body tissue, for example, as a chitin solution; (2) this chitin solution is applied as a coating onto the PTFE layer; (3) the chitin solution may be prepared by using a solvent for chitin such as a mixture of lithium chloride and dimethyl acetamide or a mixture of lithium chloride and N-methylpyrrolidone. It is preferable to dissolve chitin into the solvent containing lithium chloride of over 5 weight percent so as to obtain a solution containing chitin of 0.3 to 10 weight percent; and (4) after the chitin solution is coated onto the PTFE film, it is coagulated by immersing it into a coagulating liquid, preferably water, methyl alcohol, ethyl alcohol or acetone. After coagulation, the laminate is washed with water.

Another method is to acetylate chitosan after coating into chitin. Chitosan produced by deacetylation of chitin is readily soluble in acid. It is acetylated after forming it into a membrane.

An example is as follows: (a) chitosan is dissolved into a water solution containing acetic acid of 10 weight percent so as to obtain a solution containing chitosan of 5 weight percent; (b) the solution obtained containing chitosan is diulted with methyl alcohol to three times its volume; (c) the diluted solution obtained is coated onto the PTFE layer and left to dry; (d) after drying; the composite is swollen by immersing it into methyl alcohol containing water of 20 weight percent for about ten minutes. Then acetic anhydride (2 to 100 mole per one mole of glucosamine) is added and it is left as it is for 30 minutes; (e) the composite is immersed into a water solution containing 2 percent NaOH for 30 minutes; and (f) the composite is then washed with water and left to dry.

Chitin dissolved into a solvent may be impregnated into a PTFE membrane, as shown in FIG. 2, by applying pressure, using vacuum techniques or employing supersonic waves.

Figure 3:
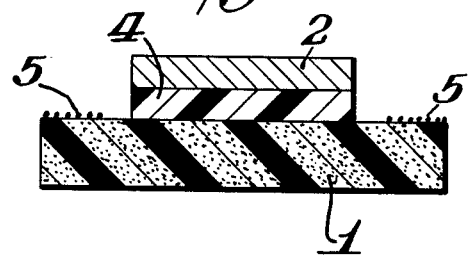
FIG. 3 is a cross-sectional view of still another embodiment of the invention.

The chitin layer 2 may be formed on the aforementioned film 1 with a water-absorbing macromolecular material 4 such as polyvinylalcohol or an acrylic acid graft-polymerized starch which will absorb blood and other liquids interposed between layer 2 and film 1, as shown in FIG. 3.

In all cases, a pressure sensitive adhesive is applied, preferably in a dot pattern, to the peripheral areas of the aforementioned porous, expanded polytetrafluoroethylene film 1 so that the film can be caused to adhere to the area surrounding the wound that it is to cover. Furthermore, therapeutic drugs or antibiotics may be included in the aforementioned chitin 2 may have a sponge-form or nonwoven-fabric-form porous structure.

The abovementioned porous, expanded polytetrafluoroethylene film is obtained by fibrilizing a polytetrafluoroethylene film by rolling or drawing as disclosed in U.S. Pat. No. 3,953,566, so that a structure is formed in which numerous micronodes are connected by countless fibrils. By making the pore size (fibril length) of this structure approximately 0.01 to 1 micron, it is possible to effectively prevent the permeation of the film by bodily fluids or body tissues. As a result, the covering material can easily be peeled from the wound to which it is applied.

The aforementioned chitin is a biotechnological material. As a tissue fiber component found in crustaceans, it fulfills the biological functions of both collagen in higher animal tissues and cellulose in higher plant tissues, and has a desirable compatibility with living cells. When this chitin is applied to a wound, it is appropriately decomposed and absorbed. By adjusting the rate of absorption, it is possible to prevent sticking to the wound and a desirable healing effect is obtained. Even when all of the chitin is absorbed, the covering material can quickly be peeled from the wound by means of the aforementioned porous, expanded polytetrafluoroethylene film 1 and replaced.

As was described above, the covering material of the present invention, which consists principally of a porous, expanded polytetrafluoroethylene film 1, fits effectively over the area of the wound. Furthermore, as a result of its porous structure, this film is both air permeable and moisturevapor-permeable. In addition, as a result of the small pores of the film and the liquid-water-repellent nature of the material itself, the film has waterproof characteristics and thus prevents the passage of bodily fluids. Similarly, the film completely prevents invasion of the wound by bacteria or small dust particles. Accordingly, the present invention provides a comfortable and desirable covering material for cuts and other wounds, which possesses waterproof characteristics and anitbacterial barrier properties.

The aforementioned chitin is generally obtained as a semitransparent or nearly transparent material. This chitin has a uniform thickness as a result of being applied to the aforementioned porous, expanded polytetrafluoroethylene film. Furthermore, this material has an appropriate tensile strength and is therefore suitable for handling. In particular, since this material can be formed into an extremely thin film, it is easy to fit over the surface of the body, and, since it is not bulky, the covering material can be applied to the fingers and will not catch on other objects as work is being performed. Since the covering material has waterproof characteristics as described above, various types of work such as cooking or laundering can be smoothly performed by a person wearing this covering material over a wound.

As described above, the present invention provides a covering material which fits appropriately over the area of a wound and which has air and moisture-vapor permeability so that the wearer feels no substantial uncomfortable dampness. Moreover, this material has waterproof characteristics and antibacterial barrier properties, and fits appropriately on the surface of the body, so that a superior therapeutic effect is obtained. Following absorption of the aforementioned chitin, the material can easily be peeled away from the wound without causing the wearer any substantial discomfort. Accordingly, the present invention has great practical merit.

While the invention has been disclosed herein in connection with certain embodiments and detailed descriptions, it will be clear to one skilled in the art that modifications or variations of such details can be made without deviating from the gist of this invention, and such modifications or variations are considered to be within the scope of the claims hereinbelow.

What is claimed is:

1. A wound dressing comprising a layer of chitin affixed to a layer of porous, expanded polytetrafluoroethylene.

2. The dressing of claim 1 wherein the chitin is laminated to the polytetrafluoroethylene.

3. The dressing of claim 1 wherein the chitin penetrates into and is impregnated in the porous polytetrafluoroethylene layer.

4. The dressing of claim 1 having a pressure sensitive adhesive applied in a dot pattern on its surface, thereby providing means to apply and secure said dressing over a wound.

5. The dressing of claim 1 wherein said porous, expanded polytetrafluoroethylene has a microstructure of nodes interconnected by fibrils wherein fibril lengths range from about 0.01 to about 1.0 micrometers.

6. The dressing of claim 1 wherein a layer of a water-absorbing macromolecular material is interposed between said chitin layer and said polytetrafluoroethylene layer.

7. The dressing of claim 6 wherein said water-absorbing macromolecular material is polyvinylalcohol.

8. the dressing of claim 6 wherein said water-absorbing macromolecular material is an acrylic acid graft-polymerized starch.

* * * * *

UNITED STATES PATENT AND TRADEMARK OFFICE
CERTIFICATE OF CORRECTION

PATENT NO. : 4,803,078
DATED : February 7, 1989
INVENTOR(S) : Mari Sakai

It is certified that error appears in the above-identified patent and that said Letters Patent is hereby corrected as shown below:

In column 3, line 26, after "chitin" and before "2", please add —film—.

In column 3, lines 26-27, after "2" and before the ".", please add —or chitin-impregnated layer 3. Moreover, the aforementioned chitin 2—.

In column 3, line 57, please change "moisturevapor-permeable" to —moisture-vapor-permeable—.

In column 4, line 2, please change "anitbacterial" to —antibacterial—.

Signed and Sealed this

Seventeenth Day of April, 1990

Attest:

HARRY F. MANBECK, JR.

*Attesting Officer*  *Commissioner of Patents and Trademarks*